(12) United States Patent
Kurze et al.

(10) Patent No.: US 9,364,581 B2
(45) Date of Patent: Jun. 14, 2016

(54) MEDICAL IMPLANT COMPRISING A BIODEGRADABLE MAGNESIUM-BASED ALLOY AND METHOD FOR ITS MANUFACTURE

(71) Applicant: DEPUY SYNTHES PRODUCTS, INC., Raynham, MA (US)

(72) Inventors: Peter Kurze, Augustusburg (DE); Thomas Imwinkelried, Seltisberg (CH); Stefan Beck, Niederdorf (CH); Dora Banerjee, Kerpen (DE); Tamara Schwarz, Bergheim (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/708,528

(22) Filed: May 11, 2015

(65) Prior Publication Data
US 2015/0238653 A1   Aug. 27, 2015

Related U.S. Application Data

(62) Division of application No. 13/331,683, filed on Dec. 20, 2011, now Pat. No. 9,050,389.

(60) Provisional application No. 61/425,294, filed on Dec. 21, 2010.

(51) Int. Cl.
A61L 27/30 (2006.01)
C01F 5/24 (2006.01)
(Continued)

(52) U.S. Cl.
CPC ............ *A61L 27/047* (2013.01); *A61B 17/80* (2013.01); *A61B 17/864* (2013.01); *A61L 27/306* (2013.01);
(Continued)

(58) Field of Classification Search
CPC ............ A61L 27/303; A61L 2310/00425; C01F 5/24
USPC ................... 427/255.23; 423/431
See application file for complete search history.

(56) References Cited

U.S. PATENT DOCUMENTS 9,050,389 B2   6/2015   Kurze et al.

FOREIGN PATENT DOCUMENTS

EP   1997522 A1   12/2008
GB   595284        12/1947
(Continued)

OTHER PUBLICATIONS

Chen et al. "Characterization and Wear Resistance of Macro-Arc Oxidation Coating on Magnesium Alloy Az91 in Simulated Body Fluids", Transactions of Nonferrous Metals Society of China, CN vol. 18, Dec. 1, 2008. pp. 361-364.*
Jonsson Atmospheric Corrosion of Magnesium Alloys: Influence of Microstructure and Environmetn. KTH Chemical Science and Engineering. Doctoral Thesis in Corrosion Science Dec. 2007.*
(Continued)

*Primary Examiner* — Cachet Sellman
(74) *Attorney, Agent, or Firm* — Baker & Hostetler LLP

(57) ABSTRACT

A medical implant comprises a biodegradable magnesium-based alloy of which at least a part of its surface layer comprises a magnesium carbonate. A method for the manufacture of a biocompatible, corrosion-inhibiting protective surface layer on a medical implant comprising a magnesium-based alloy, comprises: providing an implant comprising a magnesium-based alloy to be coated; placing the implant into a reactor chamber; exposing at least part of the surface of said implant to an atmosphere comprising humid carbon dioxide to produce a coating on the surface of the implant comprising a magnesium carbonate of the formula x $MgCO_3$ . y $Mg(OH)_2$, whereby x+y=1; removing the implant from the reactor chamber; and drying the surface of the implant.

8 Claims, 1 Drawing Sheet

(51) Int. Cl.

| | |
|---|---|
| A61L 27/04 | (2006.01) |
| A61L 27/58 | (2006.01) |
| A61L 31/02 | (2006.01) |
| A61L 31/08 | (2006.01) |
| A61L 31/14 | (2006.01) |
| A61B 17/80 | (2006.01) |
| A61B 17/86 | (2006.01) |

(52) U.S. Cl.
CPC ............... *A61L 27/58* (2013.01); *A61L 31/022* (2013.01); *A61L 31/082* (2013.01); *A61L 31/148* (2013.01); *C01F 5/24* (2013.01); *A61F 2310/00425* (2013.01); *A61L 27/303* (2013.01); *A61L 2400/18* (2013.01); *A61L 2430/02* (2013.01); *Y10T 428/265* (2015.01); *Y10T 428/31678* (2015.04)

(56) References Cited

FOREIGN PATENT DOCUMENTS

| TW | 200829511 | 7/2008 |
|---|---|---|
| WO | WO 2008/034835 | 3/2008 |

OTHER PUBLICATIONS

Xin et al "Influence of Aggressive Ions on the Degradation Behavior of Biomedical Magnesium Alloy in Physiological Environment", ACTA Biomaterialia, Elsevier, Amsterdam vol. 4 No. 6 Nov. 1, 2008 pp. 2008-2015.*

Chen et al., "Characterization and Wear Resistance of Macro-Arc Oxidation Coating on Magnesium Alloy AZ91 in Simulated Body Fluids", Transactions of Nonferrous Metals Society of China, Nonferrous Metals Society of China, CN, vol. 18, Dec. 1, 2008, pp. S361-S364.

Jonsson et al., "Corrosion Product Formation During NaCl Atmospheric Corrosion of Magnesium Alloy AZ91D", Corrosion Science, Oxford, GB, vol. 49, No. 3, Dec. 5, 2006, pp. 1540-1558.

Jonsson, Atmospheric Corrosion of Magnesium alloys: Influence of Microstructure and Environment. KTH Chemical Science and Engineering. Doctoral Thesis in Corrosion Science Dec. 2007.

Xin et al., "Influence of Aggressive Ions on the Degradation Behavior of Biomedical Magnesium Alloy in Physiological Environment", ACTA Biomaterialia, Elsevier, Amsterdam, NL, vol. 4, No. 6, Nov. 1, 2008, pp. 2008-2015.

The International Search Report and the Written Opinion of the International Searching Authority for International Patent Application No. PCT/US2011/066158 dated Mar. 27, 2012.

* cited by examiner

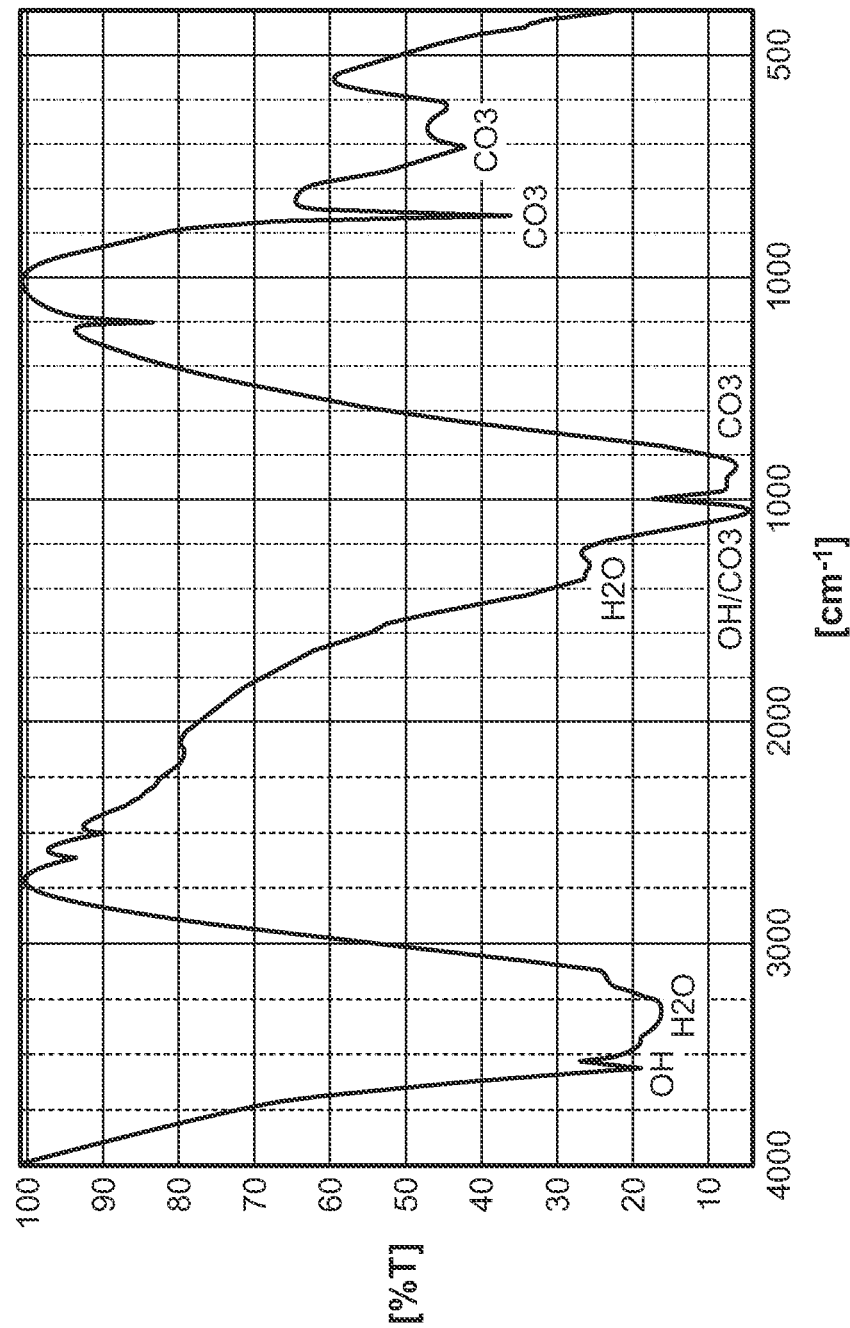

MEDICAL IMPLANT COMPRISING A BIODEGRADABLE MAGNESIUM-BASED ALLOY AND METHOD FOR ITS MANUFACTURE

CROSS-REFERENCE TO RELATED APPLICATIONS

This application is a divisional of U.S. application Ser. No. 13/331,683, filed Dec. 20, 2011 (now allowed), which claims the benefit of U.S. Provisional Patent Application No. 61/425,294 filed Dec. 21, 2010 entitled "Medical Implant Comprising A Biodegradable Magnesium-Based Alloy And Method For Its Manufacture", each of which are incorporated herein by reference in their entirety.

BACKGROUND OF THE INVENTION

The present invention generally relates to a medical implant comprising a biodegradable magnesium-based alloy and to a method for its manufacture.

BRIEF SUMMARY OF THE INVENTION

The surface of non-coated magnesium medical implants is relatively reactive and releases a peak amount of hydrogen gas after the first contact with bodily fluids. In some embodiments, the degradation of bio-resorbable magnesium implants may be slowed down by the use of adequate coatings.

In one embodiment there is a medical implant that comprises a biodegradable magnesium-based alloy of which at least a part of its surface layer comprises a magnesium carbonate. In one embodiment, the magnesium carbonate has the formula x $MgCO_3$.y $Mg(OH)_2$, whereby x+y=1. In one embodiment, x is larger than 0.3. In one embodiment, the magnesium carbonate has the formula $Mg_2[(OH)_2(CO_3)]$ .$3H_2O$. In one embodiment, the magnesium carbonate is artinite. In one embodiment, the surface layer has a thickness in the range of about 0.5 µm to about 8 µm. In one embodiment, the surface layer has a thickness in the range of about 1 µm to about 5 µm. In one embodiment, the magnesium carbonate is a basic magnesium carbonate. In one embodiment, the surface layer additionally comprises magnesium oxide MgO. In one embodiment, the magnesium carbonate has the formula $Mg[(OH)_x(CO_3)y].(H_2O)_z$, whereby x+y=2 and z=0.25 to 2.

In one embodiment, the implant is chosen from the groups of bone fixation elements, the bone fixation elements including at least one of bone plates, bone screws, surgical sutures, gut clamps, and clips for blood vessels; endo-prostheses, the endo-prostheses being in the area of hard, and soft tissues; anchoring elements for medical electrodes of pace makers, defibrillators or stents; and anchoring elements for tendon fixation in sports medicine.

In another embodiment, there is a method for the manufacture of a biocompatible, corrosion-inhibiting protective surface layer on a medical implant comprising a magnesium-based alloy, the method comprising: providing an implant comprising a magnesium-based alloy to be coated; placing the implant into a reactor chamber; exposing at least part of the surface of said implant to an atmosphere comprising humid carbon dioxide to produce a coating on the surface of the implant comprising a magnesium carbonate of the formula x $MgCO_3$.y $Mg(OH)_2$, whereby x+y=1; removing the implant from the reactor chamber; and drying the surface of the implant.

In one embodiment, the humid carbon dioxide comprising atmosphere has a relative humidity of at least 30%. In one embodiment, the gas atmosphere comprising $CO_2$ and water vapor is modified by the addition of hydrogen gas and/or gaseous hydrocarbons, in particular of methane or propane. In one embodiment, the hydrogen gas and/or gaseous hydrocarbons are added in an amount of less than 10% of the total gas content. In one embodiment, the relative humidity is 100%. In one embodiment, the relative humidity is at least about 90%. In one embodiment, the temperature in said reactor is in the range of 10° C. to 50° C. In one embodiment, the temperature in said reactor is in the range of 20° to 30° C.

In one embodiment, the concentration of the carbon dioxide is at least 50%. In one embodiment, the concentration of the carbon dioxide is at least about 90%. In one embodiment, the atmosphere is activated by heating up the atmosphere without heating up the implant. In one embodiment, the atmosphere is activated by heating up the atmosphere using microwaves. In one embodiment, the pressure in said reactor exceeds atmospheric pressure. In one embodiment, the pressure in said reactor is in the range of about 5 to about 60 bar. In one embodiment, water is added to the reactor before placing the implant into the reactor chamber. In one embodiment, the pressure in said reactor corresponds essentially to atmospheric pressure.

In one embodiment, the magnesium-based implant is coated over a time period lasting about 24 hours to about 720 hours. In one embodiment, the drying is effected at 80° C. to 130° C. In a further embodiment the method includes treating the surface of the implant with supercritical carbon dioxide prior to exposing at least part of the surface of the implant to the atmosphere comprising humid carbon dioxide. In one embodiment, the drying is effected for about 10 minutes to about 30 minutes.

BRIEF DESCRIPTION OF THE DRAWING

Exemplary embodiments of the invention will be described in the following by way of examples and with reference to the accompanying drawing in which:

FIG. 1 is a graph which illustrates an infrared spectrum of a coating obtained according to a method according to an exemplary embodiment of the invention.

DETAILED DESCRIPTION OF THE INVENTION

A number of processes are known in the art for protecting the surface of bio-degradable implants. However, many of these processes are not suitable to be used in the human body. Some of them do not fulfill the serious requirements for biocompatibility, others would be too complicated to be applied to medical implants, e.g., when filigree magnesium-based implants have to be contacted electrically when used in electrochemical procedures.

In some embodiments, the degradation of bio-resorbable magnesium implants can be slowed down by the use of adequate coatings. The surface of non-coated magnesium implants is quite reactive and releases a peak amount of hydrogen gas after the first contact with bodily fluids. The released gas can induce the formation of unwanted cavities in soft and hard tissue of the human (and animal) body. Gas pockets might be avoided if the gas release rate is kept below the transport capability of the involved tissues.

Ceramic coatings produced by spark discharge in an electrolyte (known as plasma-electrolytic coating or micro-arc process) are promising in achieving this goal. The drawback of this technology is the high energy consumption and the imperfections of the coatings at the contacting sites.

In some embodiments, the present invention provides an alternative method for manufacturing a corrosion-inhibiting coating on a medical implant which is made of biocorrodable magnesium-based material.

In some embodiments, the present invention relates to a medical implant of which at least apart of its surface layer comprises a magnesium carbonate which retards the biocorrosion of the magnesium-based alloy. In one embodiment, the surface layer is produced by exposing the surface of the implant to a gaseous atmosphere containing water and $CO_2$ as main constituents. In one embodiment, the exposure to the gaseous atmosphere leads to the formation of magneseum carbonate on the surface of the implant. The formed basic magnesium carbonate may have the benefit of initially protecting the implant surface from the aggressive chloride ions of the blood plasma and subsequently slow down the degradation of the metallic implant. In one embodiment, the surface layer is non-toxic and is expected to degrade after fulfilling its function.

In some embodiments, the present invention provides a method to passivate the surface of magnesium and magnesium alloys. In one embodiment, the magnesium implant is placed inside a container with a humid carbon dioxide atmosphere. In one embodiment, the $CO_2$-gas and the humidity react with the magnesium surface and lead to the formation of magnesium carbonate layers (e.g., in a coating on the implant). As an example, basic magnesium carbonate crystals (artinite) may be found at the implant surface after a 1 week treatment in a pressure-less atmosphere. Where no toxic components are involved, the coating is expected to exhibit good biocompatibility. In-vitro degradation tests in simulated body fluid, in some embodiments, show that the amount of liberated gas can be diminished compared to non-coated magnesium of the same lot. In one embodiment, the upper limit of liberated gas depends on the implantation site (i.e. on the tissue surrounding the implant). In vitro, it is shown, in some embodiments, that the coating delays the initial burst release and can therefore help to avoid gas pockets.

The method may be used for pure magnesium, rare earth containing magnesium alloys (e.g., WE-alloys), aluminum containing magnesium alloy (e.g., AZ-alloys, AM-alloys, AS-alloy, AE-alloys) and all kinds of other magnesium alloys (e.g., alloys with Ca, Sr, Ba etc.; amorphous alloys).

The corrosion-inhibiting coating according to embodiments of the invention is intended to provide only a temporary inhibition of the corrosive processes, so that the dissolving/disintegrating process of the magnesium-based material implanted in the human body in a physiological environment is taking place at a continuous low rate but avoiding the complete inhibition of the corrosive process.

In one embodiment, a medical implant comprises a biodegradable magnesium-based alloy of which at least a part of its surface layer comprises a magnesium carbonate.

In an embodiment of the medical implant, the magnesium carbonate is a basic magnesium carbonate.

In a further embodiment of the medical implant, the magnesium carbonate has the formula x $MgCO_3 \cdot$ y $Mg(OH)_2$, whereby x+y=1.

In a further embodiment of the medical implant, x is larger than about 0.3.

In another embodiment of the medical implant, the surface layer additionally comprises magnesium oxide MgO.

In another embodiment of the medical implant, the magnesium carbonate has the formula $Mg[(OH)_x(CO_3)_y] \cdot (H_2O)_z$, whereby x+y=2 and z=0.25–2.

In another embodiment of the medical implant, the magnesium carbonate has the formula $Mg_2[(OH)_2(CO_3)] \cdot 3 H_2O$ and preferably is artinite.

In yet another embodiment of the medical implant, the surface layer has thickness in the range of about 0.5 μm to about 8 μm. In one embodiment, the surface layer has a thickness in the range of about 1 μm to about 5 μm.

In some embodiments, the implant is chosen from the groups of:
(i) bone fixation elements, such as, for example, bone plates, bone screws, surgical sutures, gut clamps, clips for blood vessels;
(ii) endo-prostheses, prostheses in the area of hard and soft tissues;
(iii) anchoring elements for medical electrodes of pace makers, defibrillators or stents; and
(iv) anchoring elements for sports medicine, for example, tendon fixation.

For magnesium-based implants there are, in some embodiments, specific requirements for the corrosion-inhibiting layer. The mechanical load of the material during any deformation of the implant, e.g. by bending or dilating, does have an influence on the corrosion process and it has been recognized that the stress corrosion cracking is enhanced in the loaded regions. Finally, the dimensions of the filigree metallic structure have to be observed and a thin but even corrosion-inhibiting layer is to be produced.

According to a further embodiment of the invention, there is provided a method for the manufacture of a biocompatible, corrosion-inhibiting protective coating on a magnesium-based implant. Said method, in some embodiments, comprises the following steps:

A) providing an implant comprising a magnesium-based alloy to be coated;
B) placing the implant into a reactor chamber;
C) exposing at least part of the surface of said implant to an atmosphere comprising humid carbon dioxide to produce a coating on the surface of the implant comprising a magnesium carbonate of the formula x $MgCO_3 \cdot$ y $Mg(OH)_2$, whereby x+y=1;
D) removing the implant from the reactor chamber; and
E) drying the surface of the implant.

The surface of the magnesium-based implant which is to be placed into a reactor chamber as defined in step A of the method should, in some embodiments, purposefully be free from grease or oil or other impurities. In one embodiment, this is achieved by treatment of the surface with organic solvents and/or with basic aqueous solutions.

In one embodiment, the placing of the magnesium-based implant into a reactor chamber as defined step B of the method can be effected purposefully by attaching the implant to plastic fixation/holding means in order to avoid a corrosive reaction between the implant and another metal (contact corrosion) which would contaminate the surface of the implant. To this effect, the wearing of fiber-free gloves is recommended. In one embodiment, this applies also to the removing step D of the method. The final drying step E of the method can be performed in a clean air current.

It has been found that a coating produced according to the method according to embodiments of the invention is not completely inhibiting the corrosion when the coating is exposed to a physiological environment, but produces a biocorrosion (i.e. a dissolution/disintegration of the magnesium-based implant) at a significantly reduced reaction rate. Consequently, the generation of gaseous hydrogen is much smaller and the implant bed is prevented from inflammation.

In some embodiments, the methods described herein produce a conversion of the magnesium based material at its uppermost surface layer and not by adding/applying a distinct coating material to the implant surface. In some embodiments, the chemical conversion of the uppermost surface layer of the magnesium-based implant takes place in the humid carbon dioxide comprising atmosphere. The hydroxyl ions-$OH^-$ of the water in humid atmosphere may form a stable barrier layer of $Mg(OH)_2$ on the implant surface, which may in turn slowly be converted to basic magnesium carbonate by the action of the carbon dioxide gas.

When the magnesium based implant, created by the method according to embodiments of the invention, is dissolved by biocorrosion in the human body the basic magnesium carbonate is able to bind protons $H_3O^+$. In some embodiments, this guarantees that the implant bed cannot become too acidic thereby preventing a possible inflammation.

In an embodiment of the method, the humid carbon dioxide comprising atmosphere has a relative humidity of at least about 30%. In one embodiment, the humid carbon dioxide comprising atmosphere has a relative humidity of at least about 90%. In another embodiment of the method, said relative humidity is 100%.

In another embodiment of the method, the concentration of the carbon dioxide is at least about 50%. In one embodiment, the concentration of the carbon dioxide is at least about 90%.

In yet another embodiment of the method, the temperature in said reactor is in the range of about 10° C. to about 50° C. In one embodiment, the temperature in said reactor is about 20° to about 30° C. In one embodiment, the temperature in said reactor is about 25° C.

In a further embodiment of the method, the gas atmosphere comprising $CO_2$ and water vapor is modified by the addition of hydrogen gas and/or gaseous hydrocarbons. In one embodiment the gas atmosphere comprising $CO_2$ and water vapor is modified by the addition of methane or propane. By these additional gases a change in chemistry may occur by the formation of hydrides which facilitates the formation of carbonates.

In a further embodiment of the method, the hydrogen gas and/or gaseous hydrocarbons are added in an amount of less than about 10% of the total gas content.

In a further embodiment of the method, the atmosphere is activated by heating up the atmosphere without heating up the implant. In one embodiment, the atmosphere is activated by heating up the atmosphere by means of microwaves. The effect of the atmosphere may be enhanced by using different types of activation. In one embodiment, the idea is to heat up (accelerate) the gas molecules without heating up the implant. As an example, a microwave furnace might be use to shortly heat up the water molecules.

In still a further embodiment of the method, water is added to the reactor before step B. In one embodiment, the addition of water allows to obtain 100% humidity in the reactor, In another embodiment of the method, the pressure in said reactor corresponds essentially to atmospheric pressure.

In another embodiment of the method, the pressure in said reactor is exceeding atmospheric pressure and preferably is in the range of about 5 to about 60 bar.

In again another embodiment of the method, said magnesium-based implant is coated over a time period lasting about 24 hours to about 720 hours. In one embodiment, said magnesium-based implant coating duration is about 1 week.

In still another embodiment of the method, said drying is effected at about 80° C. to about 130° C. In one embodiment, drying is effected at about 80° C. for about 10 minutes to about 30 minutes.

In yet another embodiment, the method further comprises a pre-treatment step to be performed before step A and which comprises the treatment of the surface of the implant with supercritical carbon dioxide. In some embodiments, the purpose and advantage is cleaning of the surface.

Example 1

An 8-hole bone plate which can be pre-bent to fix craniomaxillo facial bone fractures made of the magnesium based material WE 43 according to ASTM B80 standard was intensively cleaned with 96% ethanol and subsequently dried in an exsiccator. The lid of the exsiccator was opened and the adaptation plates were attached individually on plastic hooks. Subsequently, the lid of the exsiccator was closed. Then the humidity of the air in the exsiccator was adjusted to 90%. The concentration of the carbon dioxide in the exsiccator was measured to be approximately 80 vol.-% which was obtained by a continuous constant flow of carbon dioxide gas at a rate of 1 liter/hour.

The adaptation plates were exposed to t is atmosphere under ambient pressure and room temperature for a period of 480 hours. After completion of the process the inflow of the carbon dioxide current was stopped, the reactor door was opened; the coated adaptation plates were removed from the reaction chamber and were dried for 20 minutes at a temperature 120° C.

The infrared spectrum of the conversion layer produced by the method according to embodiments of the invention shows the typical absorption lines of a basic magnesium carbonate with crystal water (see FIG. 1).

FIG. 1 illustrates an exemplary Fourier transform infrared spectroscopy (FTIR) spectrum where the x-axis shows the frequency as wave length (cm-1) of the infrared light and the y-axis the percentage of absorbance. In one embodiment, such a spectrum is characteristic for the absorption of infrared tight by the molecules present and can therefore be used to identify the "fingerprint" of the substance inside the coating.

The infrared spectrum obtained is almost identical to that of the naturally occurring mineral artinite $Mg_2[(OH)_2(CO_3)] \times 3H_2O$.

Example 2

Cannulated Screws for Osteosynthesis

Headless compression screws made of titanium alloy are commonly used in hand and foot surgery. These screws are cannulated (hollow) and can therefore be guided by using a Kirschner wire. The headless compression screws allow to fix bone fragments without a protruding screw head.

The magnesium version of the headless compression screw is first acid cleaned in 10% HF solution. The implant is then transferred to the upper compartment of an exsiccator. The tower compartment contains a small amount of liquid water. Air is evacuated from the exsiccator which is then flushed with $CO_2$ gas. After 1 week, the coated implant is removed, packaged and γ-sterilised prior to the implantation. The advantage of the coating technology is that the inner hole is easily accessible to the gas atmosphere. The used alloy is WZ21.

Example 3

Plate-Screw System for CMF

An 8-hole bone plate (40×5×0.9 mm) is used in combination with 2.0 mm cortex screws to fix bone fractures in the midface. The same magnesium alloy WE43 according to ASTM B80 standard is used for both implants. The implants are coated in a modified incubation chamber where humidity and $CO_2$ flow rate can be adjusted. The temperature of the chamber is 37° C. and the implants are removed after 5 days of coating time.

Example 4

Magnesium Foam

An open-pore metal foam is made of high purity magnesium. If non-treated, the large exposed surface of the implant would release a tremendous amount of hydrogen gas within the first hours of implantation.

The foam is first cleaned using supercritical $CO_2$ and then transferred to the coating chamber. The coating is done with 90% humidity under a small flow of $CO_2$. The coating time is 2 weeks. The advantage of the gaseous atmosphere is that the intricate pore structure can be coated as gas can flow through the interconnected pores.

Although the inventions and their advantages have been described in detail, it should be understood that various changes, substitutions, and alterations can be made herein without departing from the spirit and scope of the inventions as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

We claim:
1. A medical implant comprising:
a biodegradable magnesium-based alloy of which at least a part of its surface layer comprises a magnesium carbonate, wherein the magnesium carbonate has the formula:

$Mg_2[(OH)_2(CO_3)].3 H_2O$; or $Mg[(OH)x(CO_3)y].(H_2O)z$ whereby $x+y=2$ and $z=0.25$ to 2 wherein the magnesium carbonate is formed by exposing at least a part of the surface of the medical implant to an atmosphere comprising humid carbon dioxide.

2. The medical implant according to claim 1, wherein the magnesium carbonate has the formula $Mg_2[(OH)_2(CO_3)].3 H_2O$.

3. The medical implant according to claim 2, wherein the magnesium carbonate is artinite.

4. The medical implant according to claim 1, wherein the surface layer has a thickness in the range of about 0.5 μm to about 8 μm.

5. The medical implant according to claim 4, wherein the surface layer has a thickness in the range of about 1 μm to about 5 μm.

6. The medical implant according to claim 1, wherein the surface layer additionally comprises magnesium oxide MgO.

7. The medical implant according to claim 1, wherein the magnesium carbonate has the formula $Mg[(OH)x(CO_3)y].(H_2O)z$, whereby $x+y=2$ and $z=0.25$ to 2.

8. The medical implant according to claim 1, the implant being selected from the group consisting of:
(i) bone fixation elements, the bone fixation elements including at least one of bone plates, bone screws, surgical sutures, gut clamps, and clips for blood vessels;
(ii) endo-prostheses, the endo-prostheses being in the area of hard and soft tissues;
(iii) anchoring elements for medical electrodes of pace makers, defibrillators or stents; and
(iv) anchoring elements for tendon fixation in sports medicine.

* * * * *